United States Patent
Mishra et al.

(10) Patent No.: US 10,519,942 B2
(45) Date of Patent: Dec. 31, 2019

(54) METHODS OF OPERATING A PUMP TO REDUCE OR ELIMINATE PUMP BACKLASH ERRORS

(71) Applicant: Accriva Diagnostics, Inc., San Diego, CA (US)

(72) Inventors: Ajit Mishra, San Diego, CA (US); David Miers, San Diego, CA (US)

(73) Assignee: Accriva Diagnostics, Inc., San Diego, CA (US)

( * ) Notice: Subject to any disclaimer, the term of this patent is extended or adjusted under 35 U.S.C. 154(b) by 168 days.

(21) Appl. No.: 15/272,099

(22) Filed: Sep. 21, 2016

(65) Prior Publication Data
US 2018/0030980 A1 Feb. 1, 2018

Related U.S. Application Data

(60) Provisional application No. 62/367,859, filed on Jul. 28, 2016.

(51) Int. Cl.
*F04B 13/00* (2006.01)
*F04B 17/03* (2006.01)
(Continued)

(52) U.S. Cl.
CPC ............ *F04B 13/00* (2013.01); *B01L 3/0293* (2013.01); *F04B 17/03* (2013.01); *F04B 19/22* (2013.01);
(Continued)

(58) Field of Classification Search
CPC .......... F04B 13/00; F04B 17/03; F04B 19/22; F04B 2201/0201; F04B 2201/0206;
(Continued)

(56) References Cited

U.S. PATENT DOCUMENTS 3,731,679 A * 5/1973 Wilhelmson ........ A61M 5/1452
604/121
4,566,868 A 1/1986 Menzies
(Continued)

FOREIGN PATENT DOCUMENTS

| WO | 9919628 | 4/1999 | |
|---|---|---|---|
| WO | WO 9919628 A1 * | 4/1999 | .......... B01F 13/1055 |
| WO | 2015184056 A1 | 12/2015 | |

OTHER PUBLICATIONS

International Searching Authority, ISR and Written Opinion, International Application No. PCT/US2017/042492, dated Sep. 22, 2017, 14 pages.
(Continued)

*Primary Examiner* — Kenneth J Hansen
(74) *Attorney, Agent, or Firm* — Burns & Levinson LLP; Joseph P. Quinn

(57) ABSTRACT

A method of operating a pump can include advancing a stepper motor one or more additional steps in a first direction after detecting a first change in a limit sensor state corresponding to a piston reaching an end of its travel in a first direction. After advancing the stepper motor the additional step or steps in the first direction, the stepper motor can be reversed and advanced in a second direction until a second change in the limit sensor state is detected. The stepper motor can then be advanced in the second direction a predetermined number of steps associated with a full travel of the piston.

14 Claims, 8 Drawing Sheets

(51) Int. Cl.
*F04B 19/22* (2006.01)
*F04B 49/06* (2006.01)
*G01N 33/49* (2006.01)
*B01L 3/02* (2006.01)

(52) U.S. Cl.
CPC .......... *F04B 49/065* (2013.01); *G01N 33/49* (2013.01); *G01N 33/4905* (2013.01); *B01L 2200/148* (2013.01); *B01L 2400/0478* (2013.01); *F04B 2201/0201* (2013.01); *F04B 2201/0206* (2013.01); *G05B 2219/43193* (2013.01)

(58) Field of Classification Search
CPC ....... F04B 49/06; F04B 49/065; A47J 31/402; B01L 3/0293; B01L 2200/143; G05B 2219/43193
USPC .................................................. 318/685, 696
See application file for complete search history.

(56) References Cited

U.S. PATENT DOCUMENTS

| | | | |
|---|---|---|---|
| 5,302,348 A | | 4/1994 | Cusack et al. |
| 5,764,018 A | * | 6/1998 | Liepe .................... G05B 19/40 318/120 |
| 8,029,247 B2 | | 10/2011 | Cedrone et al. |
| 8,163,440 B2 | | 4/2012 | Yokozawa et al. |
| 2005/0013708 A1 | | 1/2005 | Peeler et al. |
| 2010/0320237 A1 | | 12/2010 | Raj et al. |
| 2013/0104631 A1 | | 5/2013 | Tokuo et al. |

OTHER PUBLICATIONS

International Preliminary Report on Patentability (Chapter I of the Patent Cooperation Treaty), International Application No. PCT/US2017/042492, dated Jan. 29, 2019, 7 pages.
First Office Action issued in corresponding Chinese application No. 201780046775.4, dated Nov. 4, 2019, 11 pages.

* cited by examiner

METHODS OF OPERATING A PUMP TO REDUCE OR ELIMINATE PUMP BACKLASH ERRORS

BACKGROUND

Coagulation monitoring devices are used to test a patient's blood before, during and after procedures such as cardiac surgery, cardiovascular surgery, cardiac catheterization, electrophysiology, extracorporeal membrane oxygenation, hemodialysis, etc., to test the patient's response to anti-coagulant medications such as:
Heparin
Vitamin K antogonists such as Warfarin (Coumadin)
Novel oral anticoagulants such as dabigatran, rivaroxaban, and apixaban.

Anticoagulants are a class of drugs that work to prevent coagulation (clotting) of blood. It is important for each patient to be administered the amount and type of anticoagulant that is appropriate for his/her individual physiology. Too large an amount of anticoagulants can cause uncontrolled bleeding. Too small an amount of anticoagulants can cause thrombosis (blood clotting), which can lead to heart attack (acute myocardial infraction), or stroke.

Some known point-of-care (POC) coagulation monitoring devices operate by pumping a predefined quantity of blood from a sample well into a test chamber of a cuvette. The test chamber of the cuvette can contain an activator such as silica, kaolin, diatomaceous earth, etc. Once in the test chamber, the pump can move the sample back and forth at a predetermined rate and monitor for clot formation. For example, optical detectors can be operable to detect a decrease in sample mobility, which can be indicative of clot formation.

Known POC coagulation monitoring devices suffer from a number of deficiencies, including inaccurate pumps, high pump current draw, excess pump heat, and difficulties visualizing clot formation. Clotting time measurement is a critical measurement in a number of scenarios, including treatment of stroke victims and pre-operative care. Therefore, a need exists for improvements in coagulation monitoring devices.

Platelet function tests are used to assess the ability of a patient's platelets to be activated via a specific pathway. This allows a medical professional to evaluate a patient's response to P2Y12 inhibitors such as thienopyridine's including clopidogrel (Plavix®) and prasugrel (Effient®) which are prescribed in cases of acute coronary syndrome (ACS) such as heart attack (acute myocardial infarction) and chest pain (angina). Platelet function tests can also measure activation from a variety of agonists such as arachidonic acid, epinephrine, collagen, etc.

Some known POC platelet function devices operate by pumping a predefined quantity of blood from a blood tube into one or more test chambers. These devices may be turbidimetric based optical detection systems, which measure platelet induced aggregation. For example, each test chamber can be imaged via an independent optical sensor illuminated by a dedicated emitter. The reagent is formulated to measure platelet aggregation mediated by a specific pathway (P2Y12, Arachadonic Acid, llb/llla). Light transmittance increases as activated platelets bind and aggregate fibrinogen coated beads. The instrument measures this change in optical signal and reports results in test specific Reaction Units (PRU, ARU, or PAU).

Known POC platelet function devices suffer from deficiencies similar to those described above with reference to POC coagulation monitoring devices, including inaccurate pumps, high pump current draw, excess pump heat, and difficulties visualizing platelet aggregation. Individual response to p2Y12 inhibitors is variable and adequate platelet inhibition is not assured using a common empirical dose. For example, the literature reports as many as 30% of patients do not respond to Plavix. Platelet function testing is therefore a critical measurement to ensure that each patient receives an effective dose of appropriate drugs. Therefore, a need exists for improvements in platelet function devices. In some instances, embodiments described herein can be suitable for improving platelet function devices and/or coagulation monitoring devices.

SUMMARY

Some embodiments described herein relate to a method of operating a pump, such as a pump of a coagulation monitoring device or a platelet function device, that can reduce or eliminate backlash errors and improve pumping accuracy and accuracy of test results. Known pumps and known methods of operating pumps are subject to backlash errors associated with changes in direction of the piston. When a pump motor changes direction, the piston may not immediately respond, which can cause significant pumping errors. In instruments such as coagulation monitoring devices and/or platelet function devices, pumping errors can significantly reduce the accuracy of test results.

According to an embodiment described in the present application, a method of operating a pump can include advancing a stepper motor one or more additional steps in a first direction after detecting a first change in a first limit sensor state corresponding to a piston and/or sample reaching an end of its travel in a first direction. Similarly stated, the stepper motor can be configured to "overshoot" (or attempt to overshoot) the first limit sensor after the limit sensor indicates that the piston and/or sample has reached the end of its travel. After advancing the stepper motor the additional step or steps in the first direction, the stepper motor can be reversed and advanced in a second direction until a second change in the first limit sensor state is detected. Similarly stated, the stepper motor can be advanced in the second direction until the first limit sensor indicates that the piston and/or sample has begun to move away from it. The stepper motor can then be advanced in the second direction by either a predetermined number of steps associated with a full travel of the piston or until a first change in a second limit sensor state is detected. In this way, the method can include verifying that any backlash error has been resolved or overcome before the predetermined number of steps, associated with an appropriate and/or consistent travel of the piston and/or sample are applied, which can improve pumping accuracy.

DETAILED DESCRIPTION

Figure 1:
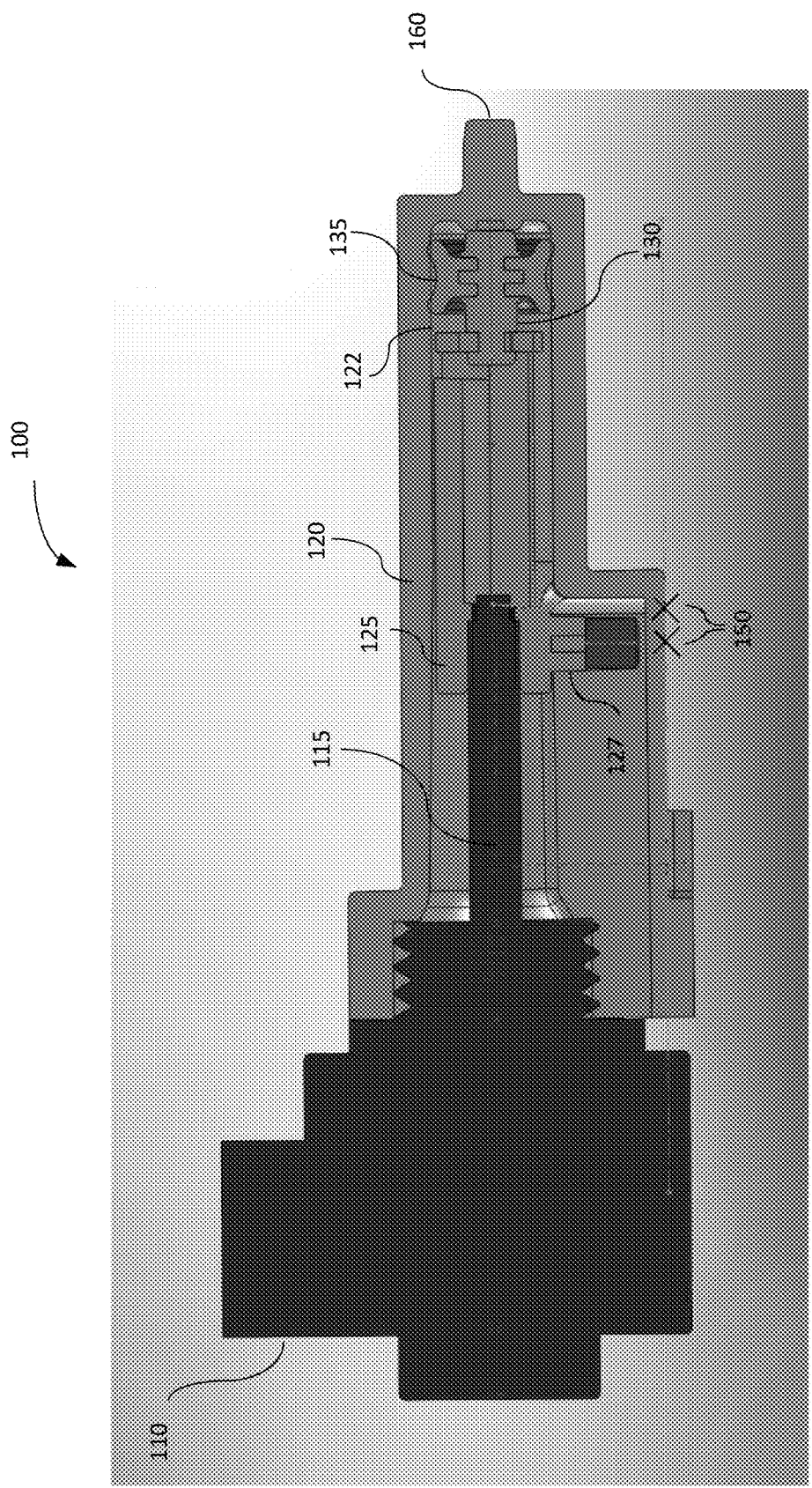
FIG. 1 depicts a pump, according to an embodiment.

Some embodiments described herein relate to methods of operating a pump, such as a piston pump driven by a stepper motor. The pump can be a portion of a medical device, such as a POC coagulation monitoring device or a platelet function device. Measurements produced by such devices can be sensitive to small pumping errors. Similarly stated, maintaining precise control of pump travel in such devices can be important to producing accurate data.

One known method for operating a pump is to advance a stepper motor a predetermined number of steps in a first direction, then advancing the stepper motor the predetermined number of steps in the second direction and then repeating. Such a method assumes that with an equal number of steps applied, the piston travels equal distances in both the first direction and the second direction. A second known method for operating a pump is to advance a stepper motor in a first direction until a first limit sensor is tripped, then advancing the stepper motor in a second direction until a second limit sensor is tripped and then repeating. The assumptions underlying these known methods, however, are faulty. Pumps can experience backlash errors when changing direction, resulting in motor steps that do not move the piston. In addition, pistons can overshoot limit sensors, resulting in larger piston travel than indicated by limit sensor. Some embodiments described herein relate to methods of operating pumps that reduce and/or eliminate backlash error, improve the consistency of piston stroke length, and/or identify pumping errors which can decrease the accuracy of data and/or can be indicative of a malfunction.

Some embodiments described herein relate to a method of operating a pump. The pump can be fluidically coupled to a test device and used to move a sample in the test device. In some embodiments, the test device can be a cuvette and/or can be disposable. An instrument containing the pump and test device can include a first limit sensor and a second limit sensor. For ease of description, the first limit sensor can be configured to sense when a sample within the test device and/or the piston reach a fixed position at a "front" end portion of the test device and/or a "front" end portion of the pump. The second limit sensor can configured to sense when the sample within the test device and/or the piston reach a fixed position at a "back" end portion of the test device and/or on a "back" end portion of the pump. It should be understood that this is for ease of description only, and that the first limit sensor can be located on the back end portion of the test device and/or pump and the second limit sensor can be located on the front end portion of the test device and/or pump. Similarly stated, the first limit sensor and the second limit sensor can be located at fixed positions at opposite end portions of the test device and/or pump and configured to change state when the piston and/or sample reach fixed positions. In this way, the first limit sensor and the second limit sensor can collectively be configured to detect when the piston and/or sample has traveled an appropriate distance for the test being performed by the instrument.

According to one embodiment, a method can include detecting a first change in the state of the first limit sensor. The first change in the state of the first limit sensor can indicate that the piston and/or sample has moved away from the fixed position and/or front end portion of the test device and/or pump on its way to the back end portion of the test device and/or pump. The stepper motor can be advanced in the backwards direction until a first change in the state of the second limit sensor is detected. The first change in the state of the second limit sensor can indicate that the sample and/or piston has reached the back end portion of the test device and/or pump. While the stepper motor is advanced in the backward direction (e.g., before the first change in the state of the second limit sensor is detected), the number of steps taken by the motor between the change in the first limit sensor state being detected and the first change in the state of the second limit sensor state can be counted and/or recorded. After the first change in state of the second limit sensor is detected, the stepper motor can be advanced at least one additional step in the backward direction before reversing the stepper motor and advancing the stepper motor in the forward direction. The stepper motor can then be advanced in the forward direction until a second change in state of the second limit sensor is detected. The second change in state of the second limit sensor can indicate that the sample and/or piston has moved away from the back end portion of the test device and/or pump on its way to the front end portion of the test device and/or pump. After the second change in state of the second limit sensor is detected, the stepper motor can be advanced in the forward direction until a second change in the state of the first limit sensor is detected and/or until the number of steps that was counted and/or recorded between when the first change in the first limit sensor state was detected and when the first change in the state of the second limit sensor state was detected. The number of pump steps counted and/or recorded between the first change in the first limit sensor state and the first change in the second limit sensor state can be compared to the number of pump steps counted and/or recorded between the second change in the second limit sensor state and the second change in the first limit sensor state. If a difference between the number of pump steps counted and/or recorded between (1) the first change in the first limit sensor state and the first change in the second limit sensor state and (2) the number of pump steps counted and/or recorded between the second change in the second limit sensor state and the second change in the first limit sensor state exceeds a threshold, an error can be reported.

According to another embodiment, a method can include advancing a stepper motor one or more additional steps in a first direction after detecting a first change in a first limit sensor state corresponding to a piston and/or sample reaching an end of its travel and/or an end portion of a pump and/or test device in a first direction. Similarly stated, the stepper motor can be configured to cause the piston and/or sample "overshoot" (or attempt to overshoot) the first limit sensor after the first limit sensor indicates that the piston and/or sample has reached the end of its travel and/or reached an end portion of the pump and/or test device. After advancing the stepper motor the additional step or steps in the first direction, the stepper motor can be reversed and advanced in a second direction until a second change in the first limit sensor state is detected. Similarly stated, the stepper motor can be advanced in the second direction until the first limit sensor indicates that the piston and/or sample has begun to move away from it. The stepper motor can then be advanced in the second direction a predetermined number of steps associated with a full travel of the piston and/or until the sample causes a second limit sensor to change state.

According to another embodiment, a method can include recording a number of steps taken by a stepper motor during a first transit from a first (e.g., front) limit sensor to a second (e.g., back) limit sensor. When a first change in a state of the back limit sensor is detected, which can indicate that the piston has reached the back of the pump and/or a sample has reached an back end portion of a test device, the stepper motor can be advanced one or more additional steps to move the piston and/or sample towards the back of the pump/test device. Similarly stated, the stepper motor can be configured to overshoot (or attempt to overshoot) the back limit sensor. The stepper motor can then be reversed and advanced to move the piston and/or sample towards the front of the pump/test device. After a second change in the back limit sensor is detected, which can indicate that the piston and/or sample has begun to move towards the front of the pump/test device, the stepper motor can advance the number of steps recorded when the stepper motor moved the piston from the front limit sensor to the back limit sensor. Similarly stated, after the back limit sensor changes state to indicate that the piston and/or sample has begun to move, which may only occur after any backlash has been resolved and/or overcome, the stepper motor can advance the same number of steps moving the piston and/or sample from the back of the pump/test device to the front of the pump/test device as was recorded when the piston and/or sample moved from the front of the pump/test device to the back of the pump/test device. In an alternative embodiment, after the second change in the back limit sensor is detected, the stepper motor can advance until a change in the front limit sensor is detected.

FIG. 1 depicts a pump 100, according to an embodiment. The pump 100 can be operable to pump a predefined quantity of blood from a sample well into a test chamber of a cuvette and/or move blood back and forth within a test chamber of a cuvette. The pump 100 includes a motor 110, a pump housing 120, and a piston 130.

In some embodiments, the motor 110 is a stepper motor, but the motor 110 can be any other suitable motor. The motor 110 can be coupled to the piston 130 via a motor shaft 115. The motor shaft 115 can be coupled to the piston 130 via a threaded connection to an adapter 125 having an anti-rotation feature 127 including a permanent magnet. Thus, the motor 110 and the adapter 125 can collectively form a linear motor such that extension and retraction of piston 130 can be effectuated by rotation of the motor shaft 115. In embodiments where the motor 110 is a stepper motor, the linear displacement of the piston 130 can be precisely controlled via the number of pulses applied to the motor 110. In addition or alternatively, positional sensors 150, such as Hall effect sensors, can be operable to monitor the position of the adapter 125, which can provide confirmation that the piston 130 has moved.

The piston 130 can travel within the pump housing 120 and a piston seal 135 can create a substantially fluid-tight seal against the interior wall 122 of the interior bore of the pump housing 120. For example and as described in further detail herein, the piston seal 135 can be overmolded such that, in an unbiased configuration, the piston seal has a larger diameter than the diameter of the pump housing 120 defined by the interior wall 122. Within the pump housing 120, at least a portion of the piston seal 135 can deform such that the substantially fluid-tight seal is maintained. Thus, when the piston 130 moves within the pump housing 120, fluid (such as blood) can be moved into or out of the pump housing 120 via an outlet 160.

As discussed above, known pumps used for POC coagulation monitoring devices and/or platelet function devices suffer from a number of drawbacks. In particular, the amount of torque required to move the piston in some known pumps (and the accompanying power draw and waste heat produced) can be unacceptably high. For example, some known pumps maintain a seal between a piston and an interior wall of a pump housing using an o-ring or similar gasket that is compressed against the interior wall according to Gland design. When the Gland design is used, the compression of the gasket increases the torque required to move the piston, and small variations within manufacturing tolerances can significantly increase the compression of the gasket and piston's resistance to movement.

Figure 2:
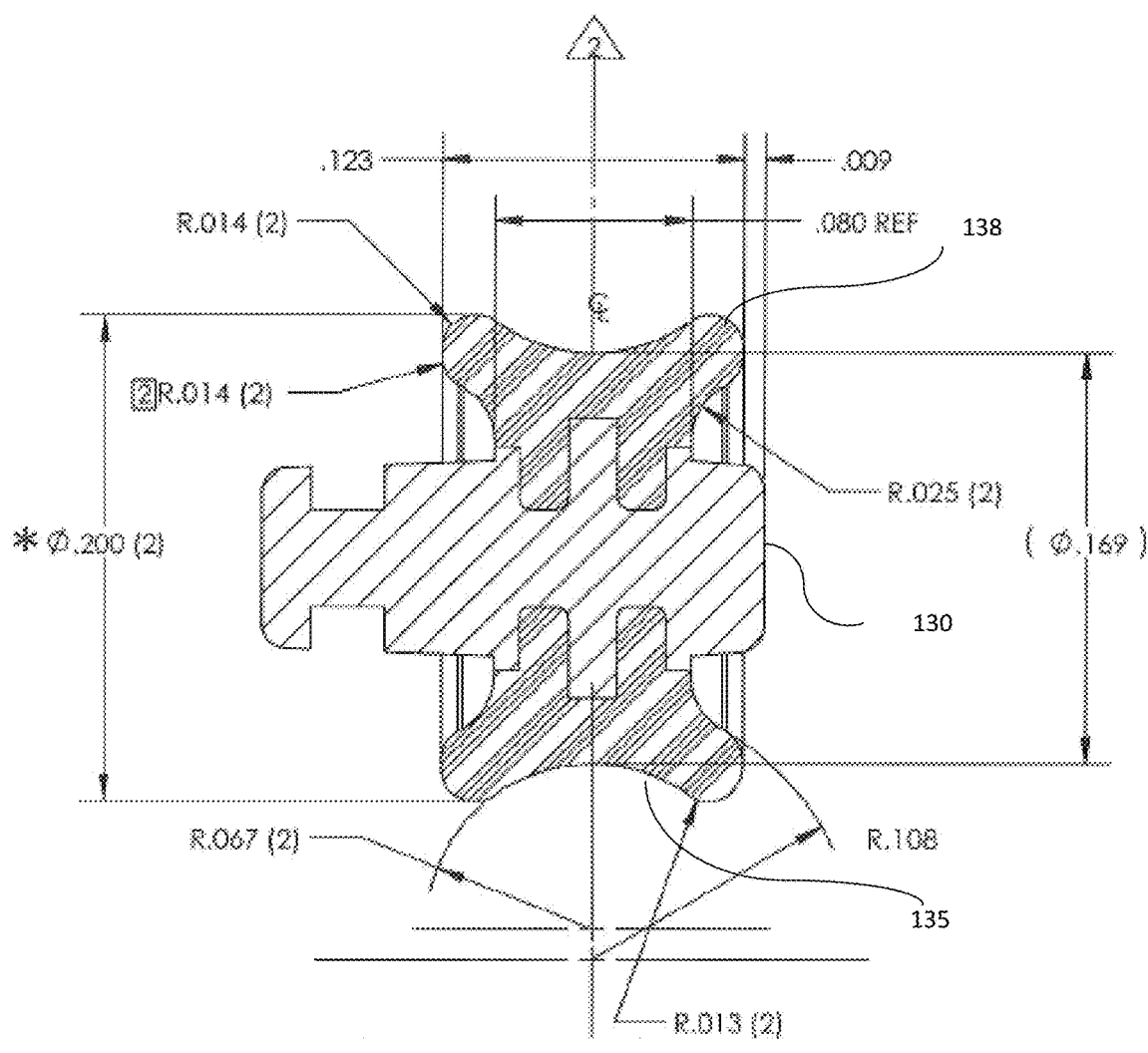
FIG. 2 depicts a piston seal, according to an embodiment.

In some embodiments, such as shown in detail in FIG. 2, the piston seal 135 can have two projections 138 or wings which elastically deflect within the pump housing 120, such that the radial force between the piston seal 135 transmitted from the piston seal 135 to the piston 130 is reduced as compared to a Gland design. As a result, decreased torques relative to the Gland design can be effective to move the piston 130. In addition or alternatively, grease or other suitable lubricant can be deposited between projections 138, further reducing friction, power consumption, and/or waste heat while maintaining and/or improving a fluid-tight seal.

Figure 3:
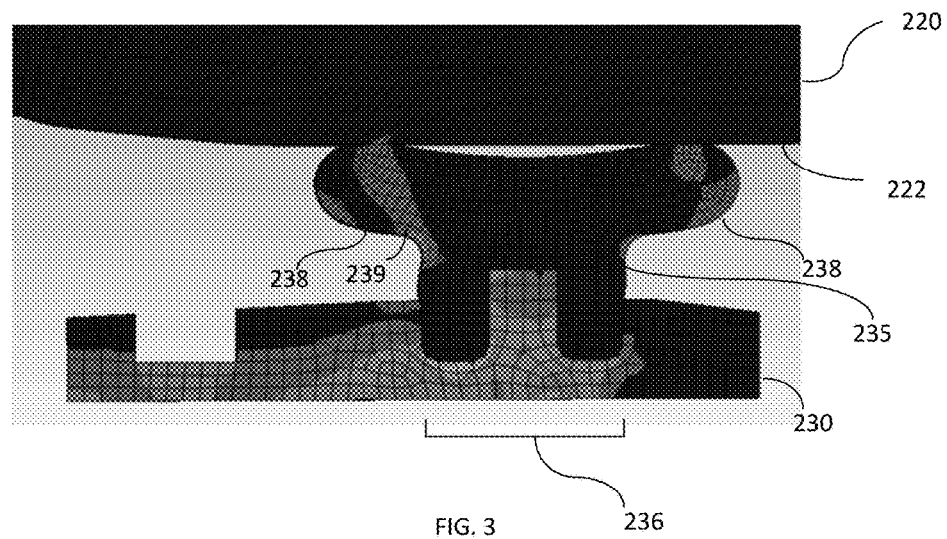
FIG. 3 depicts a finite element analysis of the piston seal of FIG. 2 disposed within a pump housing.

FIG. 3 is a finite element analysis of a piston seal 235 forming a seal against an interior wall 222 of a pump housing 220. The piston seal 235, the pump housing 220, and the interior wall 222 can each be similar to the piston seal 135, the pump housing 120, and the interior wall 122 shown in FIGS. 1 and 2 and discussed above. As shown, elastic deformation of the piston seal 235, particularly of wings 238, produces the sealing force between the seal 235 and the inner wall 222. Region 239 at the root of wing 238 illustrates this elastic deformation. Known gaskets, such as quadrings, do not produce such radial flexion. In particular, the length of wings 238 relative to the clearance between piston 230 and inner wall 222 differs from known gaskets. For example, in one embodiment, each wing 238 can have a length of 0.123 approximately (e.g., +/−10%) inches, a base 236 of the gasket can have a width of approximately 0.080 inches. A distance between the locations at which the wings 238 contact the inner wall 222 can be approximately 0.100 inches. Seal 235 can differ from known gaskets, which are typically compressed such that induced stresses are transmitted through the central region of the gasket (e.g., a geometric center), rather than being substantially confined to the wings 238 and roots 239, as shown in FIG. 3. For example, in some embodiments, a central portion of seal 235 (e.g., a geometric center) may experience stresses and/or strains less than 10% of the maximum stresses and/or strains, which are concentrated in wings 238. In some instances, the maximum stress of piston seal 235 can be approximately 22 psi, which can be substantially lower than an o-ring or quad-ring compressed according the Gland design, which can experiences stress of 200 psi or more.

Figure 4:
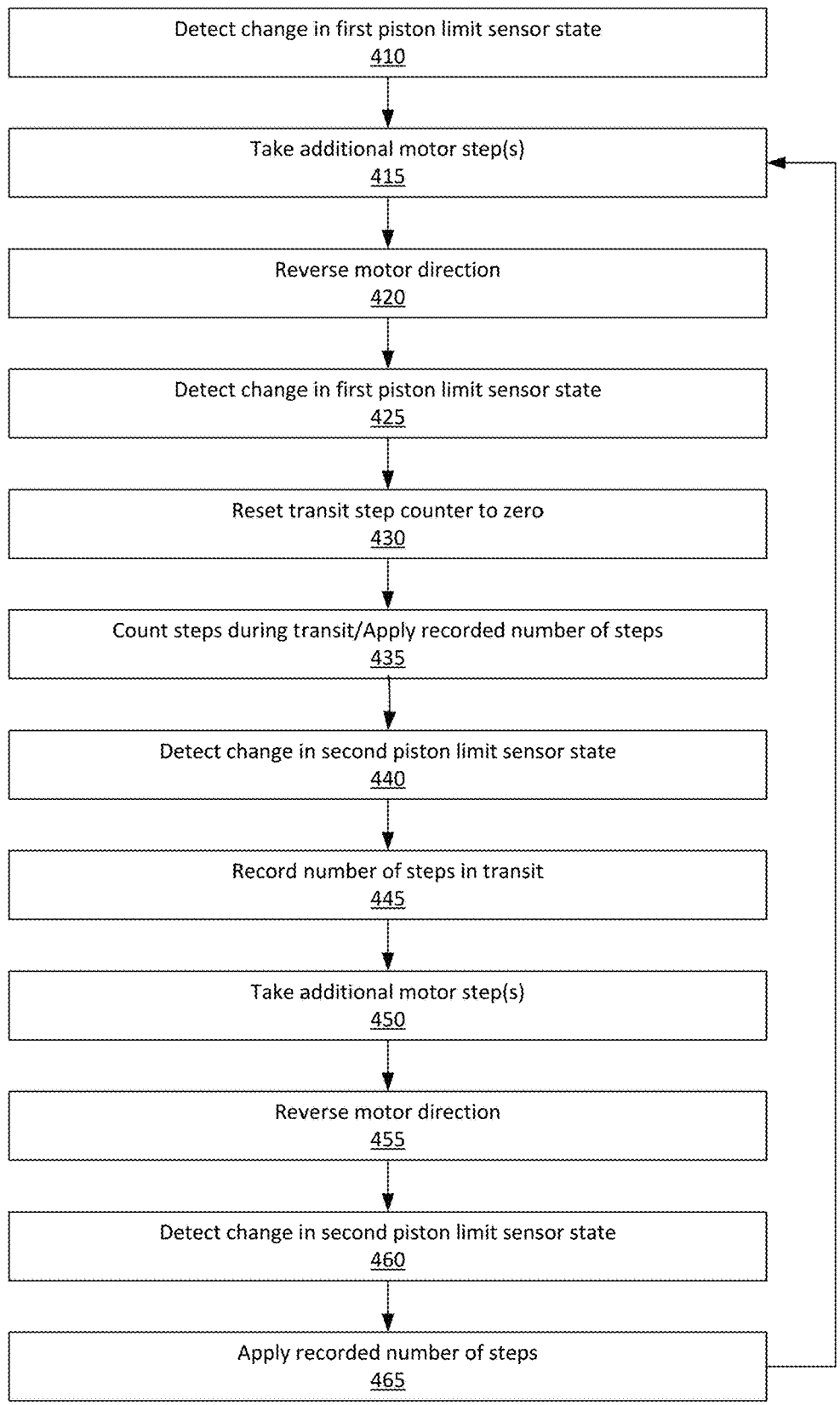
FIG. 4 is a flowchart of a method of improving pumping accuracy, according to an embodiment.

In addition, obtaining an accurate sample volume and/or precise control over moving the sample while performing a blood clotting measurement or platelet function measurement can be important factors in obtaining an accurate and/or reproducible measurement. Precise control of the movement and/or position of a piston and/or a sample driven by the piston can influence the accuracy of the test. In particular, with some known pumps, errors can accumulate at the beginning and/or end of piston movement, when the piston and/or sample reaches the end of its travel, and/or when the piston and/or sample changes direction. For example, some known pumps are susceptible to backlash error in which the motor takes several steps before the piston and/or sample begins to move, particularly when the pump changes direction. Some embodiments described herein relate to a method for reducing or eliminating such backlash error. FIG. 4, is a flow chart of a method for reducing or eliminating pump backlash error. Such a method can be performed by a pump, such as pump 100 shown and described above. In addition or alternatively, such a method can be a computer implemented method, stored in a memory and/or executed by a processor, which can be electrically coupled to a pump motor and/or pump position sensor.

At 410, a change in a state of a first limit sensor can be detected. The change of the state of the first limit sensor can indicate that the piston has reached a fixed location at an end-portion its travel and/or that a sample being driven by the piston has reached a fixed location within a test device. After the change in the state of the first piston limit sensor is detected, at 410, the motor can take one or more additional steps, at 415, before the motor direction is reversed, at 420. Similarly stated, the motor and piston can be configured to overshoot (or attempt to overshoot) the first limit sensor.

After the motor reverses, at 420, another change in the first limit sensor state can be detected, at 425. The change in state of the first limit sensor, at 425 can indicate that the piston and/or sample is moving and any extra motor steps needed to overcome a backlash have been successful. Each step after the change in the first limit sensor state is detected, at 425, can be counted until a change in a second limit sensor state is detected, at 440. The change in the second piston limit sensor state detected, at 440, can be an indication that the piston has reached a fixed location at an end-portion its travel and/or that a sample being driven by the piston has reached a fixed location within a test device in the direction opposite the first limit sensor. Similarly stated, the first limit sensor can be configured to change state when the piston is retracted and the second limit sensor can be configured to change state when the piston is extended, or vice versa. The first limit sensor and the second limit sensor can each be configured to detect when the piston and/or the sample has reached a mechanical and/or preconfigured limit.

The number of steps between the change in the first limit sensor state being detected, at 425, and the change in the second limit sensor state being detected, at 440, can be recorded (e.g., stored in memory) at 445.

After the change in the state of the second limit sensor is detected, at 440, before reversing direction, at 455, the motor can take one or more additional steps, at 450. Similarly stated, the motor and piston can be configured to overshoot (or attempt to overshoot) the second limit sensor.

After the motor reverses, at 455, another change in the second limit sensor state can be detected, at 460. The change in state of the second limit sensor, at 460 can indicate that the piston and/or sample is moving and any extra motor steps needed to overcome a backlash have been successful. At 465, the number of steps recorded at 445 can be applied. In this way, the method described with reference to FIG. 4 can be operable to assure that the same number of motor steps is applied during each stroke of the piston after any potential backlash has been resolved.

This technique can be repeated in a similar fashion, for example, until a clot is detected. For example, after the recorded number of steps has been applied at 465, one or more additional steps can be applied, at 415, before the motor reverses direction, at 420. After the motor reverses direction, at 420, the transit step counter can be reset to zero, at 430, after a change in the first limit sensor is detected, at 425. The change in the state of the first limit sensor state can indicate that the piston and/or sample is moving towards the second limit sensor and any potential backlash has been resolved. The same number of steps as was originally recorded at 445 can be applied such that the piston travels the same distance with each stroke.

It is expected that each time the recorded number of steps is applied a limit sensor will change states. In some instances, if a limit sensor changes state before the recorded number of steps has been applied or if a limit sensor does not change state after the recorded number of steps has been applied, an error signal can be produced. For example, in an instance where a limit sensor changes state before the recorded number of steps are applied, a difference between the recorded number of steps and the number of steps applied before the limit sensor changed states can be computed. If the difference is greater than a threshold value, an error can be reported. Similarly, in an instance where the recorded number of steps is applied and a limit sensor has not changed states, surplus steps can be applied until a limit sensor state change is detected. If the number of surplus steps is greater than a threshold value, an error can be reported.

In addition or alternatively, the discrepancies in the number of steps from the first limit sensor to the second position limit sensor can be tabulated and an error signal can be produced if the discrepancies are above a threshold value. For example, if a limit sensor changes state before the recorded number of steps has been applied, the routine can be shortened and one or more additional motor steps can be applied before the motor reverses direction and the number of unneeded steps can be recorded. Then, after the limit sensor changes state for a second time indicating any backlash has been overcome and/or resolved, either the original number of steps can be applied or the number of steps from limit sensor to limit sensor in the last stroke can be applied. Similarly, if the number of steps recorded at 445 are applied and no change in limit sensor state is detected, additional steps can be applied until a limit sensor state occurs and the number of additional steps required can be recorded.

As described above, the pump can continue to transit until a clot is detected. A clot can be detected by imaging a chaplet of blood. The chaplet of blood can be moved within a channel of a cuvette, test device, and/or any other suitable by a pump, such as the pump 100 shown and described above with reference to FIGS. 1 and 2 according to the method described with reference to FIG. 4. In particular, the method described with reference to FIG. 4 can improve measurements of the transit of the chaplet and half-transit measurements, improving the accuracy of clotting time assays relative to methods that do not reduce or eliminate backlash errors.

Figure 5:
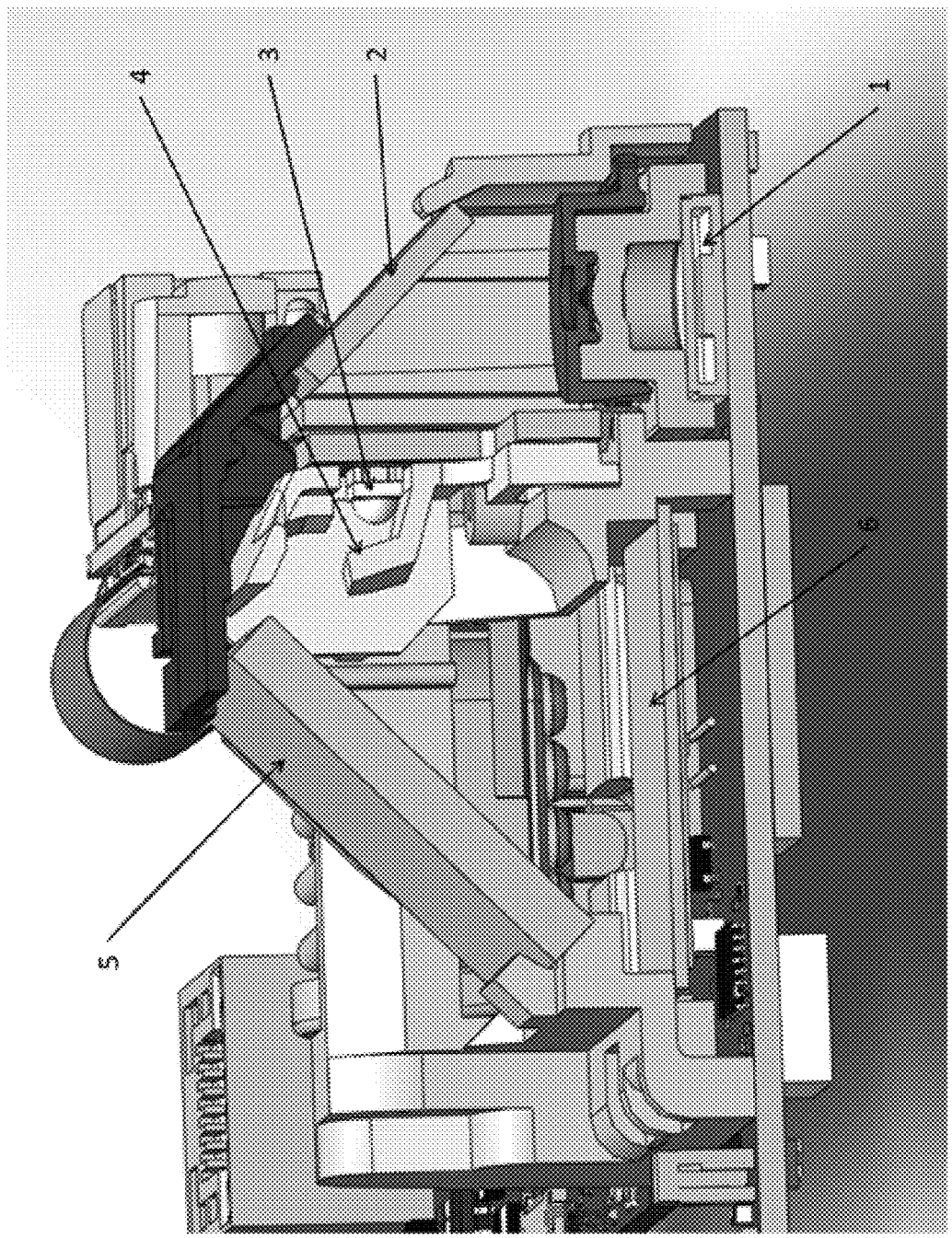
FIG. 5 an optical system suitable for detecting clot formation, according to an embodiment.

FIG. 5 depicts an optical system 500 suitable for detecting clot formation. The optical system 500 includes an optical detector 1, a light source 3, and an optical diffuser 4. Some known POC coagulation monitoring devices use a light source and an optical detector to determine when a clot has formed. Known devices, however, suffer from a number of deficiencies. In particular, the light source of known devices typically directly illuminates a target, which can produce undesirable glare resulting in visual artifacts when the target is imaged by an optical detector, decreasing measurement accuracy. In addition or alternatively, relatively large geometries may be employed by known devices in an effort to reduce glare (e.g., the light source may be positioned a relatively large distance from target). Such large geometries increase the size of the instrument and may make a handheld device impossible or impracticable.

The optical system 500 remedies the deficiencies of known instruments by illuminating a target 6 (e.g., containing a chaplet of blood) with diffuse light, which allows the instrument to maintain a compact geometry and relatively small overall size. As shown, a diffuser 4 is positioned in front of light source 3. The diffuser can be constructed of light colored (e.g., white) and/or translucent plastic or any other suitable material. In this way, light produced by the light source 3, which can be a light emitting diode, laser, or any other suitable source of illumination, can be scattered by diffuser 3 and/or light emanating from the light source 3 can be prevented from directly illuminating target 6, which can reduce or eliminate glare on the target 6.

Figure 6A:
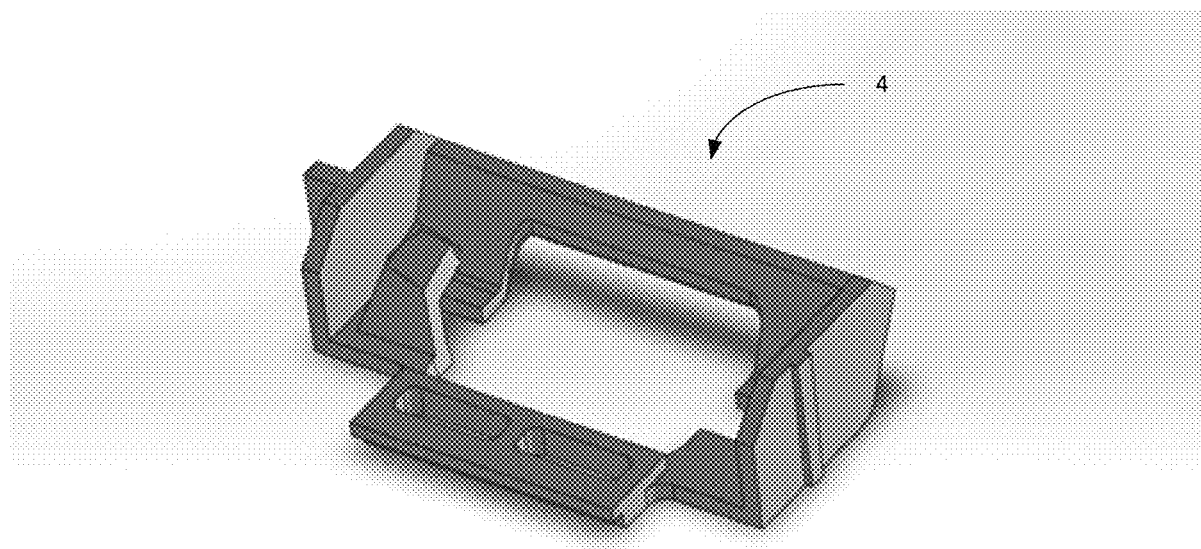
FIGS. 6A-6C depict optical diffusers, according to various embodiments.
Figure 6B:
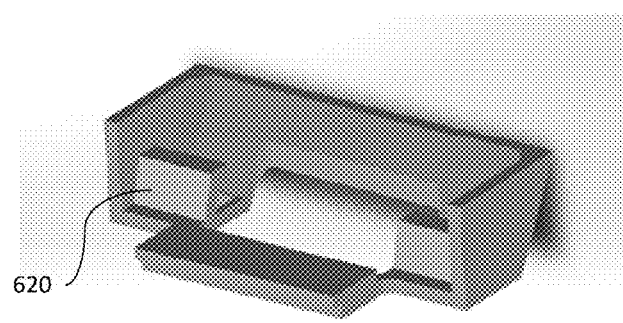
Figure 6C:
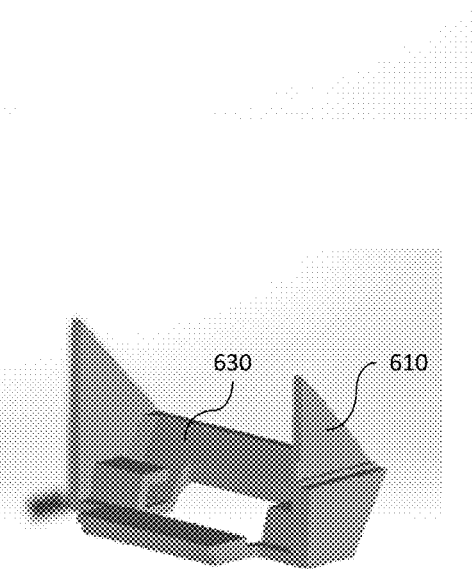

The target 6 can then be imaged by the optical detector 1, which can be for example, a charge coupled device, a complementary metal-oxide semiconductor, etc. The optical detector 1 can optionally include one or more lenses. Similarly stated, the optical detector 1 can be a camera. Mirrors 2 and 5 can reflect an image of target 6 onto optical detector 1, which can increase the focal length and/or field of view of the camera (e.g., such that an entire length of a substantial portion of the length of the target 6 can be imaged) while maintaining a compact device suitable for hand-held operation. FIG. 6A depicts the diffuser 3, according to an embodiment. FIGS. 6B and 6C depict diffusers according to alternate embodiments. The diffusers depicted in FIGS. 6B and 6C demonstrate that diffusers can have alternate geometries, such as optional side panels 610, variations in dispersion arm 620 angles, and/or variations in upper diffuser surface angles.

Figure 7:
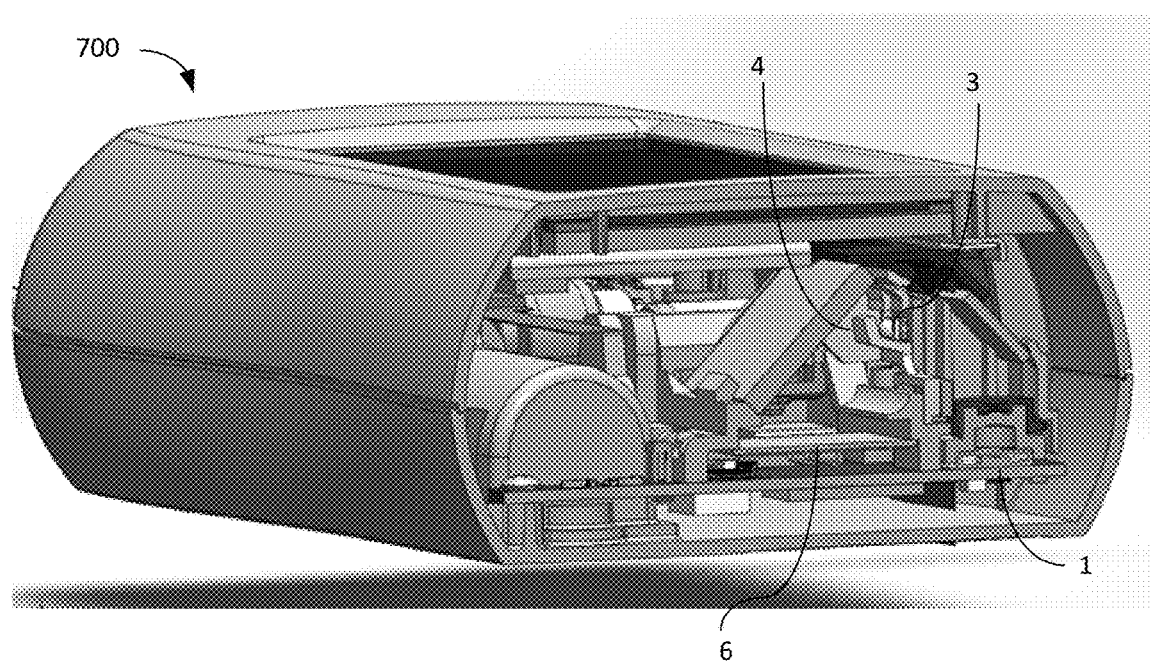
FIG. 7 depicts optical system within a coagulation monitoring device, according to an embodiment.

FIG. 7 depicts optical system 100 within a POC coagulation monitoring device 700, according to an embodiment.

POC coagulation monitoring devices, such as the coagulation monitoring device 700 shown and described above with reference to FIG. 7, can include hardware and/or software (stored in memory and/or executing on a processor) operable to be configured to run one or more tests, execute one or more tests autonomously or semi-autonomously, log test results, collect patient identifiers, operator identifiers, reagent identifiers, and so forth. Known POC coagulation monitoring devices and/or platelet function devices are generally stand alone instruments and an institution (e.g., a hospital) may have a large number of such devices. In known systems configuration of each device may be performed by connecting the device to a single computer via a serial or similar connection. A risk therefore exists that different instruments may be configured differently, reducing reproducibility. Alternatively, some known systems administer multiple devices using a central server that can configure multiple instruments. A central server, however, presents a single point of failure and increases capital and operational costs, system complexity, and ongoing administration and support. A need therefore exists for an instrument configuration manager that can configure multiple devices without relying on a central server architecture.

The POC coagulation monitoring devices and/or platelet function devices described in the present application can include a browser-based configuration manager. For example, a browser-based configuration manager can be stored in memory and/or executed by a processor of a POC coagulation monitoring device. The browser-based configuration manager can be a web application.

Figure 8:
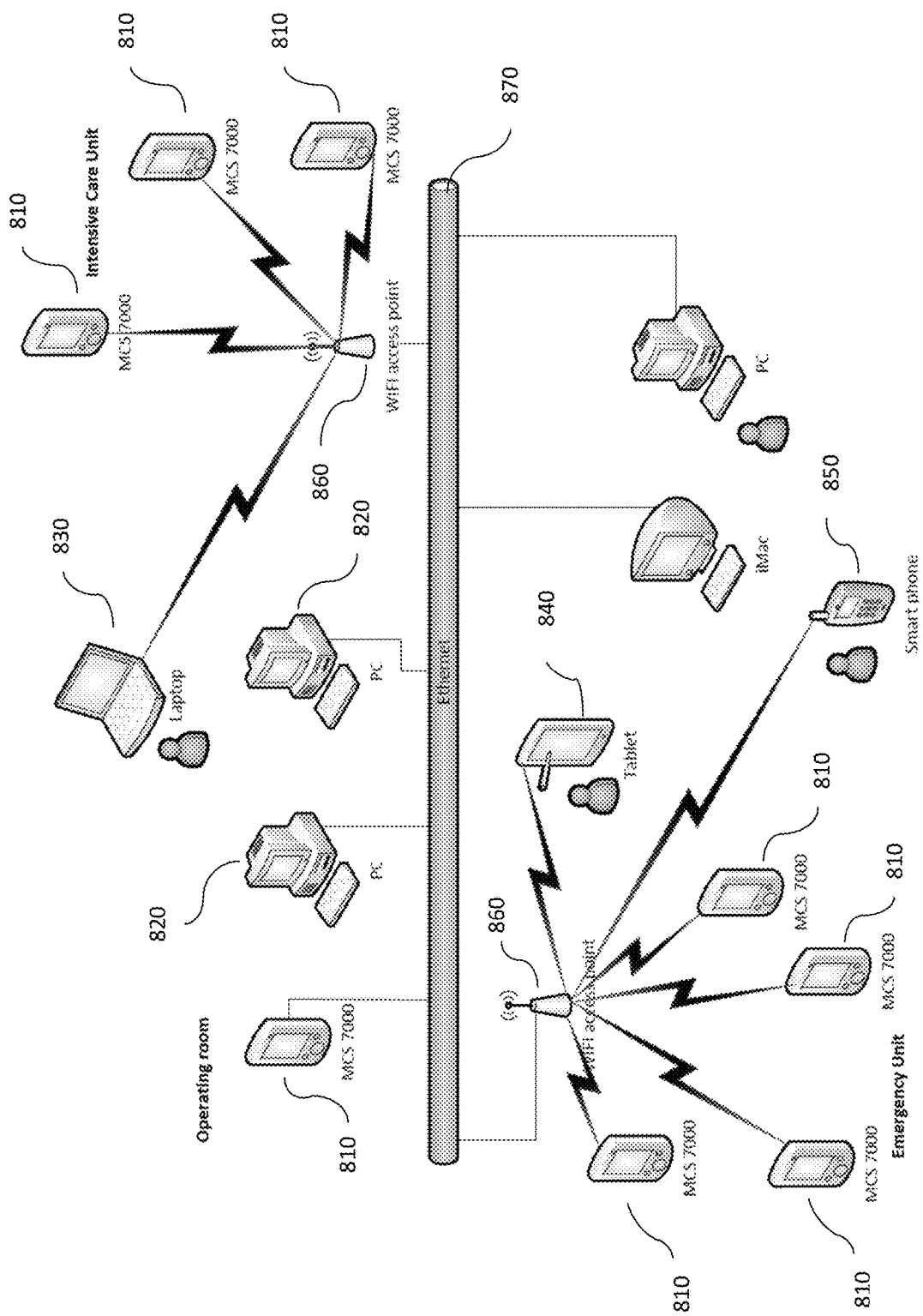
FIG. 8 is a schematic illustration of multiple coagulation monitoring devices suitable for being managed via browser-based configuration manager, according to an embodiment.

As shown in FIG. 8, the browser-based configuration manager residing on one or more coagulation monitoring devices 810 can be operable to communicate with one or more desktop computers 820, laptop computers 830, tablet computers 840, smartphones 850, and/or any other suitable computing entity (also referred to herein as compute device(s)) via a wireless gateway 860 (e.g., a WiFi access point) and/or via a wired network 870 (e.g., an Ethernet network, an intranet, the Internet, etc.). One or more compute devices can be configured to communicate with the browser-based configuration manager residing on the coagulation monitoring devices 810. For example, a web browser (stored in memory and/or executing on a processor) residing on a compute device can be operable to broadcast, narrowcast, and/or multicast configurations to one or more of the coagulation monitoring devices 810. In this way, one or more coagulation monitoring device 810 can be configured remotely using a robust web interface, for example, by a clinician and/or administrator. Such a web interface may be more intuitive and/or flexible than an input/output interface of a relatively small handheld coagulation monitoring device. Moreover, the browser-based configuration manager can eliminate the need for a central server or a special-purpose program or application to be installed on compute devices, which may be discouraged and/or prohibited by institutional information technology policies.

Figure 9:
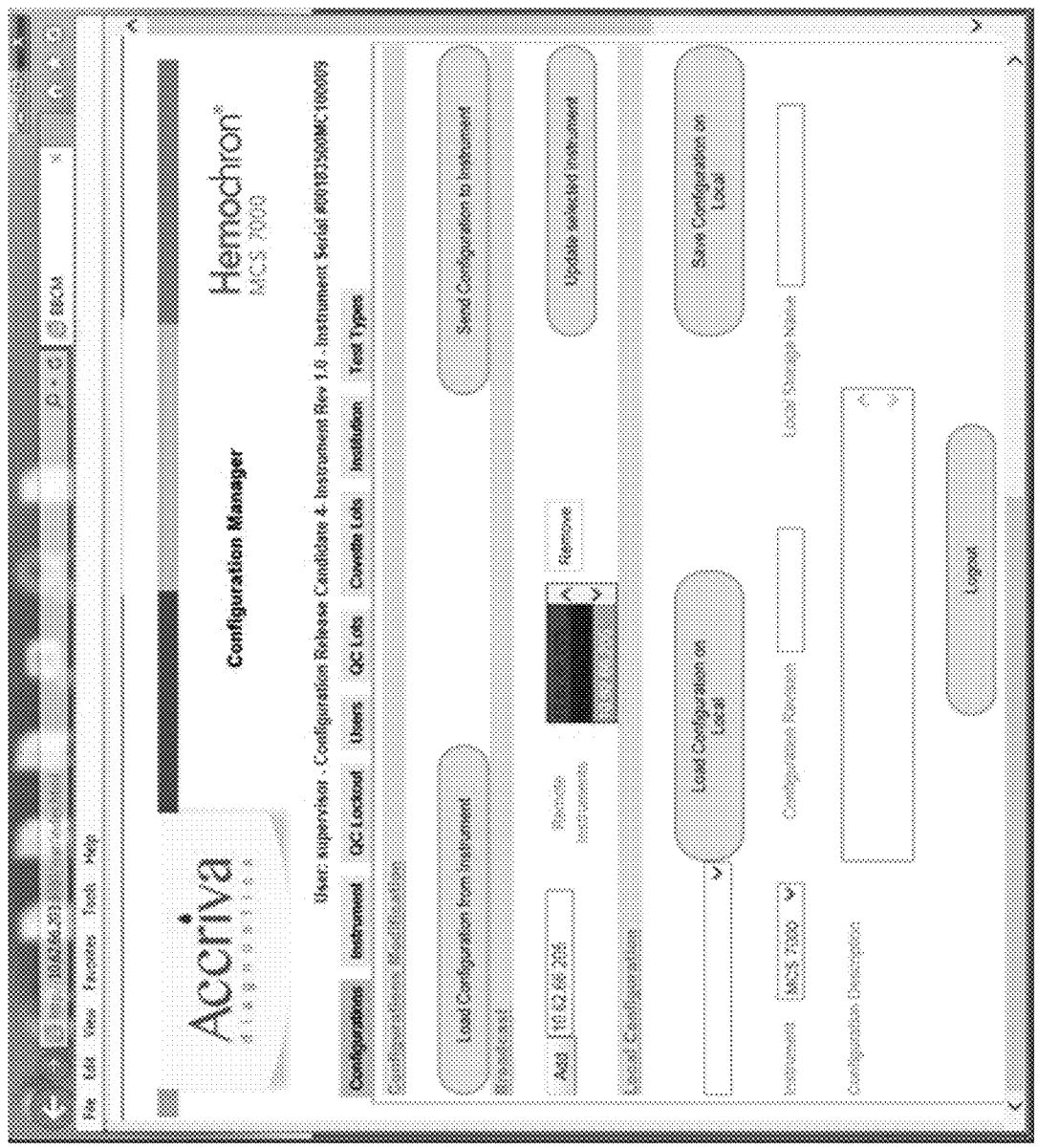
FIG. 9 illustrates a user interface of a browser-based configuration manager, according to an embodiment.

FIG. 9 illustrates a user interface of the browser-based configuration monitor, which is shown being executed (by a processor) of a compute device via Microsoft's® Internet Explorer® browser. As shown, the browser-based configuration monitor can be operable to interact with and/or monitor the status of any number of coagulation monitoring devices 810, which are shown identified by IP address, but can be identified by any other suitable identifier such as location, user- or administrator-assigned identifier, model number, serial number, etc. The status of each coagulation monitoring device can be displayed, for example, by color coding identifiers (e.g., red for disconnected, green for connecting, blue for selected, etc.) or any other suitable technique.

Using the browser-based configuration monitor, a user can add or remove devices from being monitored and/or select one or more devices to receive a configuration update. When configuring devices, parameters can be set using the browser interface and transmitted to each coagulation monitor device 810, which can be remote from the compute device. In instances where multiple coagulation monitoring devices 810 are configured, the browser-based configuration manager can assure that each selected coagulation monitoring devices 810 is configured with the same parameters.

The browser-based configuration monitor can be operable to configure one or more coagulation monitoring devices 810 in a manual, semi-automatic, or automatic process. For example, in a manual process, a user can select one or more coagulation monitoring devices 810, supply the appropriate parameters, and transmit the parameters to the one or more coagulation monitoring devices 810, for example, by clicking a button. In an automatic process, all connected devices or a subset of all devices can be displayed and updated with the latest configuration. For example, all devices in a cardiac catheterization lab can be automatically selected and updated with the most recent cardiac catheterization lab configuration.

In addition or alternatively, configuration settings (e.g., set by a remote compute device via the browser-based configuration monitor) can be viewed and/or modified at a coagulation monitoring device. Similarly stated, a clinician can override or modify a group setting for a particular test using the input/output interface of the coagulation monitoring device 810 and/or can modify a setting for a particular coagulation monitoring device using the clinician's personal smartphone 850 or other compute device.

Some known medical devices can perform a Power On Self Test (POST) to verify instrument functionality when devices are turned on. Many medical devices, however, are not "powered on" during routine operation. For example, a medical device may be powered up and not powered down or unplugged for hours or days. When a device is in service for an extended period of time since the most recent POST, a risk develops that one or more hardware components or systems has failed and/or that memory has become corrupted between the POST and when an instrument is used to analyze a sample. Known instruments perform POSTs by verifying the overall functionality of the system, for example, by performing a simulated sample analysis or dry run. Such known POSTs generally take a substantial period of time (e.g., 45 seconds to several minutes) to perform. Performing such a POST in between sample analyses or before a sample is analyzed is not generally feasible. A need therefore exists to verify the operation of an instrument prior to a sample analysis without introducing lengthy delays or down time.

In some embodiments, a medical instrument, such as the POC coagulation monitoring devices and/or platelet function devices described above, can perform an electronic quality control check of the device's measurement pathway(s) and critical electronics, immediately prior to analyzing a sample. Such an electronic quality control check can test components individually and/or in parallel, rather than testing the system as a whole, such as by performing a dry run, as is typical for known POSTs. In this way, the time to verify instrument reliability can be reduced significantly to, for example, ten seconds or less.

The electronic quality control check can verify the operation of the instrument by testing internal voltages, analytic firmware (e.g., via a cyclic redundancy check), assay definition file (e.g., via a cyclic redundancy check), calibration (e.g., via a cyclic redundancy check), factory settings (e.g., via a cyclic redundancy check), batteries, camera, the operation of the real time clock, external voltage supply, serial communications, and/or any other suitable hardware, software, and/or subsystems.

During an electronic quality control check a quality control program (stored in memory and/or executing on a processor) can receive independent feedback from tested element(s). For example, DC voltage can be fed, via independent inputs, to a quality-control check analog-to-digital converter, which can measure the voltage and determine (e.g., individually) if each DC voltage is within acceptable ranges (e.g., using software stored in memory and/or executing on a processor). In addition or alternatively, tested elements can be cross checked against each other. For example, an output from a camera can be analyzed with field of view illumination turned on and with field of view illumination turned off. In this way, a malfunction in either the camera or the illumination can result in an error being generated if, for example, the output of the camera does not change as expected when the illumination is turned on.

In the event of an error, the user can be notified via the POC coagulation monitor input/output and/or a signal can be sent to a browser-based or other suitable configuration monitoring system. In some instances, the coagulation monitor can prevent further operation of the device until all parameters and/or critical parameters are within predetermined operational ranges.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, and not limitation. For example, some aspects described in the present application are described with respect to POC coagulation monitoring devices. It should be understood that some aspects described herein have applicability to applications other than POC coagulation monitoring devices. In particular, the diffuser described above with reference to FIGS. 5-7 or a similar diffuser can be used in a platelet function instrument or any other suitable instrument in which an optical detector images a target illuminated by a light source positioned a relatively short distance from the target. As another example, the browser-based configuration manager and/or the electronic quality control check described above can be implemented by any suitable device, such as a platelet function instrument.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While the embodiments have been particularly shown and described, it will be understood that various changes in form and details may be made.

Although various embodiments have been described as having particular features and/or combinations of components, other embodiments are possible having a combination of any features and/or components from any of embodiments where appropriate.

What is claimed is:

1. A method to reduce or eliminate pump backlash errors, comprising:
   providing a system comprising a pump having a stepper motor coupled to a piston, said system further comprising a first limit sensor displaced apart from a second limit sensor;
   advancing, with the motor, the piston in a forward direction in the pump;
   detecting a first change in the first limit sensor state to indicate that the piston has reached a fixed forward location at an end-portion of its forward travel in the pump;
   using the motor to advance the piston one or more additional steps in the forward direction beyond the fixed forward location after the first change in the first limit sensor state is detected;
   using the motor to advance the piston in a rearward direction opposite the forward direction after the one or more additional steps; and,
   detecting a second change in the first limit sensor state indicating that the piston is moving in the rearward direction from the fixed forward location in the pump and that backlash errors associated with changes in direction of the piston have been reduced or eliminated.

2. The method of claim 1, further comprising:
   detecting the second change in the first limit sensor state after advancing the stepper motor in the rearward direction a portion of the number of steps; and
   reporting an error based on a difference between the number of steps and the portion of the number of steps being greater than a threshold.

3. The method of claim 1, further comprising:
   counting a number of steps while advancing the piston in the rearward direction until a first change in a second limit sensor state is detected indicating that the piston has reached a fixed rearward location at an end-portion of its rearward travel in the pump;
   using the motor to advance the piston one or more additional rearward steps in the rearward direction beyond the fixed rearward location after the first change in the second limit sensor state is detected;
   using the motor to advance the piston in the forward direction after the one or more additional rearward steps; and
   detecting a second change in the second limit sensor state after advancing the piston in the forward direction indicating that the piston is moving in the forward direction from the fixed rearward location in the pump and that backlash errors associated with changes in direction of the piston have been reduced or eliminated.

4. The method of claim 1, further comprising advancing the stepper motor in the forward direction the number of steps after advancing the stepper motor in the rearward direction the number of steps.

5. A non-transitory computer readable media having software encoded thereon, the software configured to to cause the processor to:
   detect a first change in a first limit sensor state corresponding to a piston, driven by a stepper motor, reaching an end of its travel in a forward direction;
   advance the piston one or more additional steps in the forward direction after detecting the first change in the first limit sensor state;
   reverse the piston in a rearward direction after the one or more additional steps;
   detect a second change in the first limit sensor state; and
   reverse the piston in the rearward direction a predetermined number of steps associated with a full travel of the piston.

6. The non-transitory computer readable media of claim 5, wherein the software is further configured to the processor to:
   detect a change in a second limit sensor state after the stepper motor is advanced in the rearward direction the predetermined number of steps associated with the full travel of the piston.

7. The non-transitory computer readable media of claim 5, wherein the software is further configured to cause the processor to:
   detect a change in a second limit sensor state after the stepper motor is advanced in the rearward direction the predetermined number of steps associated with the full travel of the piston; and
   advancing the piston by the stepper motor in the forward direction the predetermined number of steps associated with the full travel of the piston after detecting the change in the second limit sensor state.

8. A method to reduce or eliminate pump backlash errors, comprising:
   (i) recording a number of steps taken by a stepper motor between a change in a first limit sensor state being detected and a change in a second limit sensor state being detected, during a transit of a piston driven by the stepper motor in a rearward direction from the first limit sensor to the second limit sensor;
   (ii) detecting a first change in said change in the state of the second limit sensor;
   (iii) advancing the piston one or more additional steps by the stepper motor in the rearward direction;
   (iv) advancing the piston in a forward direction opposite the rearwared direction until a second change in the state of the second limit sensor is detected;
   (v) advancing the piston in the forward direction the number of steps by the stepper motor after the second change in the state of the second limit sensor is detected; and
   (vi) advancing the piston in the rearward direction the number of steps by the stepper motor after the piston has been advanced the number of steps in the forward.

9. The method of claim 8, further comprising:
   advancing the piston in the rearward direction until the change in the state of the first limit sensor is detected before advancing the piston in the rearward direction the number of steps by the stepper motor.

10. The method of claim 8, further comprising:
    detecting the first change in the state of the first limit sensor after advancing the piston in the forward direction the number of steps;
    advancing the piston an additional step in the forward direction after detecting the first change in the state of the first limit sensor; and
    advancing the piston in the rearward direction after advancing the piston the additional step in the forward until the second change in the state of the first limit sensor is detected before advancing the piston in the rearward direction the number of steps by the stepper motor.

11. The method of claim 8, further comprising:
advancing the piston an additional step in the forward direction before advancing the piston in the rearward direction the number of steps; and
advancing the piston in the rearward direction until a change in the state of the first limit sensor is detected before advancing the piston in the rearward direction the number of steps.

12. The method of claim 8, further comprising repeating the steps (i) through (vi).

13. The method of claim 8, wherein the stepper motor is coupled to the piston, the stepper motor and the piston being components of a pump of a medical instrument.

14. The method of claim 8, wherein:
the stepper motor is configured to move the piston between the first limit sensor and the second limit sensor; and
the piston is configured to move a volume of sample within a coagulation monitoring device or a platelet function test device.

* * * * *